United States Patent [19]

Hata et al.

[11] 4,058,601

[45] Nov. 15, 1977

[54] METHOD FOR TREATING ALCOHOLISM

[75] Inventors: Shun-ichi Hata, Yokohama; Koji Mizuno, Tokorozawa; Yasuho Nishii, Niiza; Etsuko Mitsuishi, Tokyo; Motoharu Shiba, Ohmiya, all of Japan

[73] Assignee: Chugai Seiyaku Kabushiki Kaisha, Tokyo, Japan

[21] Appl. No.: 592,341

[22] Filed: July 1, 1975

[30] Foreign Application Priority Data

Nov. 7, 1974 Japan .................................. 49-78732

[51] Int. Cl.² .......................................... A61K 31/70
[52] U.S. Cl. ................................................ 424/180
[58] Field of Search ......................... 424/10, 251, 180

[56] References Cited

U.S. PATENT DOCUMENTS

| 3,852,433 | 12/1974 | Tamura | 424/180 |
| 3,852,435 | 12/1974 | Tamura | 424/180 |

FOREIGN PATENT DOCUMENTS

| 4,260M | 4/1966 | France | 424/251 |

OTHER PUBLICATIONS

J.A.C.S., vol. 81 (3032–3035) 1959.

*Primary Examiner*—Frederick E. Waddell
*Attorney, Agent, or Firm*—Browdy and Neimark

[57] ABSTRACT

A pharmaceutical composition for reducing the alcohol content or slowing the rate of increase thereof in the blood and inhibiting the accumulation of neutral lipid in the liver containing a uridine diphosphate as an effective ingredient and a method of the use thereof are disclosed.

16 Claims, No Drawings

METHOD FOR TREATING ALCOHOLISM

This invention relates to a pharmaceutical composition and a method of use thereof; particularly it relates to a pharmaceutical composition containing a uridine diphosphate as an effective ingredient for prevention and treatment of alcoholism and a method of use thereof.

Ethanol has been generally taken as an alcoholic drink, but it often causes acute and chronic alcoholism. The intake of a large amount of alcoholic drinks in a short period of time depresses the central nervous system and, thus, causes acute alcoholism such as drunkenness, dead drunkenness and coma. When taking a large amount of alcoholic liquor regularly becomes a habit, certain serious physical and mental disorders known as chronic alcoholism result. In these cases, it has been observed that the amount of neutral lipid accumulated in the liver is unusually high and this becomes a cause of liver disorder.

An object of this invention is to provide a pharmaceutical composition for prevention and treatment of alcoholism, and another object of this invention is to provide a method of treating alcoholism by the use of the pharmaceutical composition for prevention and treatment of alcoholism.

Other objects of this invention will be self-evident from the description hereinbelow.

In accordance with this invention, alcoholism in human beings can be treated and prevented by the administration of a uridine diphosphate.

One embodiment of this invention is a pharmaceutical composition for prevention and treatment of alcoholism which comprises a pharmaceutically acceptable carrier and as an effective ingredient, a uridine diphosphate in an amount sufficient to realize the prevention and treatment of alcoholism.

In accordance with this embodiment, a uridine diphosphate can be administered in the form of a preparation for oral administration or as a parenteral injection. For oral administration, tablet, granule, powder, suspension and lemonade are preferable, and the powder or granules may be put in capsules. The tablets, granules or powder are prepared by a conventional means from a uridine diphosphate with a conventional pharmaceutically acceptable carrier such as lactose, starch, dextrine, sucrose, crystalline cellulose, kaolin, calcium carbonate, talc and the like. A suspension is prepared by suspending the uridine diphosphate in an oil such as corn oil or olive oil, and lemonade is prepared by dissolving it in an aqueous solution of citric acid, tartaric acid or the like. For the preparation of parenteral injection, a uridine diphosphate is dissolved in an aqueous solution isotonized with sodium chloride, potassium chloride or the like and the solution is charged in an ampule and the ampule is melt-sealed. As an alternate method, the solution was placed in a vial and lyophilized. The amount of the uridine diphosphate in the pharmaceutical composition should be in an amount sufficient to realize treatment and prevention of alcoholism. In general, in the preparation for oral administration, such as tablet, granule, powder, capsule, suspension or lemonade, the effective ingredient may be present in an amount of from 10 to 5,000 mg, preferably 50 to 500 mg per dose. On the other hand, for parenteral injection, the active ingredient may be present in the amount of 10 to 1,000 mg, preferably 50 to 500 mg per dose.

The uridine diphosphates which are useful for this invention are uridine-5'-diphosphate and uridine-3'-diphosphate, and they may be the free form or a metallic salt form, the metal being preferably sodium, potassium, lithium or the like.

The pharmaceutical composition for prevention and treatment of alcoholism is useful not only for acute alcoholism but also for chronic alcoholism.

Another embodiment of this invention is a method for preventing and treating alcoholism in human beings by the administration of a pharmaceutical composition for prevention and treatment of alcoholism comprising an effective amount of a uridine diphosphate and a pharmaceutically acceptable carrier.

In accordance with this embodiment, a pharmaceutical composition described in the first embodiment of this invention is used as it is and the method comprises administering the composition to orally or by injection or any other proper route to human beings.

That is, the prevention of acute alcoholism may be realized by oral administration of the pharmaceutical composition defined above, such as tablet, granule, powder, capsule, suspension or lemonade, or by intravenous or intramuscular injection of the composition in the form of parenteral injection just before or at the time of intake of alcoholic drinks. In order to treat acute alcoholism, such as drunkenness, dead drunkenness or coma, the pharmaceutical composition is administered orally by use of the preparation for oral administration, or intravenously or intramuscularly by the use of the preparation for parenteral injection. In this case, the administration of the composition may be repeated every several hours to keep uridine diphosphate in blood at a high level with better results.

Since a uridine diphosphate is very low in toxicity on human beings, a considerable amount of the active ingredient may be administered for treatment of acute alcoholism. However, from the safety and economic as medicine, it is advantageous to be administered the active ingredient in an amount orally 300 mg/kg. body weight per day or 30 mg/kg. body weight per day by the parenteral injection.

The method for prevention of acute alcoholism in accordance with this invention can be applied for treating and preventing chronic alcoholism. In other words, prevention of acute alcoholism by the use of the pharmaceutical composition according to this invention is effective to prevent chronic alcoholism. Since it is very difficult to have chronic alcoholic abstain from alcoholic drinks, the administration of the composition prevents the worsening the symptoms of chronic alcoholism. The composition, therefore, can also be used for the prevention and treatment of chronic alcoholism.

When the pharmaceutical composition of this invention is used for the purpose of the prevention of alcoholism, the accumulation of neutral lipids in liver which are to be observed during alcoholism is inhibited and also alcohol level in blood is not increased rapidly. When the composition is used for the treatment, the alcohol level in blood is lowered smoothly to ease drunkenness, dead drunkenness or coma.

This invention is further illustrated by the following Examples, but they are not to be construed as limiting the scope of this invention.

EXAMPLE 1

Inhibiting Action for Accumulation of Neutral Lipid in Liver

The Sprague Dawley strain male rats weighing 180±30 g which had been fed rat food commercially available as CLEA CE-2 and prevented from eating food for 16 hours just before the experiment was started were divided into groups of 10 rats each. Each rat was orally administered with disodium uridine-5'-diphosphate (UDP-2Na) as a suspension in corn oil in a dose of 100 mg/kg body weight. Thirty minutes after the administration, each rat was orally administered with ethanol as a 50% aqueous solution in a dose of 6 g/kg. body weight and, 24 hours after the administration, the liver was taken out and an amount of neutral lipid contained therein was determined by the Van Handel and Zilver-Smit method. For control, a glucose aqueous solution having a caloric content equivalent to the same amount of ethanol was used instead of ethanol.

The results are shown in Table 1.

Table 1

| Administration | Neutral Lipid in Liver (mg/g) | % inhibition |
|---|---|---|
| Corn oil + Glucose | 11.47 ± 4.99 | — |
| Corn oil + Ethanol | 40.27 ± 9.25 | — |
| UDP . 2Na + Ethanol | 12.69 ± 7.85 | 95.7 |

EXAMPLE 2

The Sprague Dawley strain male rats weighing 260±30 g which had been fed rat food commercially available as CLEA CE-2 and prevented from eating food for 12 hours just before the experiment were divided into groups each of 10 - 13 members each. Each rat was orally administered disodium uridine-5'-diphosphate (UDP-2Na) in the form of a suspension in corn oil in an amount 100 mg/kg body weight. Thirty minutes after the administration, ethanol as a 50% aqueous solution was orally administered in a dose of 6 g/kg. body weight and then behavior of the rat was observed over 24 hours.

The results obtained are shown in Table 2.

Table 2

| Administration | Time after the administration of alcohol (hrs.) | Behaviour Deep Sleep (heads) | Lying Flat (heads) | Normal Walking (heads) | Righting Reflex − (heads) | + (heads) |
|---|---|---|---|---|---|---|
| Corn oil + Ethanol | 3 | 4 | 3 | 3 | 5 | 5 |
| | 6 | 4 | 4 | 2 | 5 | 5 |
| | 9 | 2 | 5 | 3 | 2 | 8 |
| | 12 | 0 | 1 | 9 | 0 | 10 |
| | 18 | 0 | 0 | 10 | 0 | 10 |
| UDP . 2Na + Ethanol | 3 | 1 | 5 | 7 | 1 | 12 |
| | 6 | 1 | 8 | 4 | 1 | 12 |
| | 9 | 0 | 7 | 6 | 0 | 13 |
| | 12 | 0 | 0 | 13 | 0 | 13 |
| | 18 | 0 | 0 | 13 | 0 | 13 |

EXAMPLE 3

The Sprague Dawley strain male rats weighing 160±30 g which were fed rat food commercially available as CLEA CE-2 and prevented from eating food for 12 hours just before the experiment was started. Each rat was administered with ethanol as a 50% aqueous solution in a dose of 6 g/kg body weight. Thirty minutes after the administration, the rat was orally administered with a suspension of disodium uridine-5'-diphosphate (UDP-2Na) in corn oil in a dose of 100 mg/kg. body weight based on UDP-2Na. The behavior of the rat was observed over 24 hours after the last administration.

The results obtained are shown in Table 3.

Table 3

| Administration | Time after the administration of alcohol (hrs.) | Behaviour Deep Sleep (heads) | Lying Flat (heads) | Normal Walking (heads) | Righting Reflex − (heads) | + (heads) |
|---|---|---|---|---|---|---|
| Ethanol + Corn oil | 3 | 3 | 5 | 0 | 3 | 5 |
| | 6 | 5 | 3 | 0 | 5 | 3 |
| | 9 | 3 | 3 | 2 | 2 | 6 |
| | 13 | 0 | 2 | 6 | 0 | 8 |
| | 18 | 0 | 0 | 8 | 0 | 8 |
| Ethanol + UDP . 2Na | 3 | 1 | 6 | 4 | 1 | 10 |
| | 6 | 1 | 7 | 3 | 2 | 9 |
| | 9 | 1 | 6 | 4 | 1 | 10 |
| | 12 | 0 | 1 | 10 | 0 | 11 |
| | 18 | 0 | 0 | 11 | 0 | 11 |

EXAMPLE 4

Measurement of Alcohol Level in Blood

In this Example, Sprague Dawley strain female rats (weighing 150±20 g) divided into groups of 9 - 12 members each were used.

After abstention from food overnight each rat was orally administered disodium uridine-5'-diphosphate (UDP-2Na) in the form of a physiological saline solution in a dose of 100 mg/kg. body weight as an effective ingredient and, 30 minutes after the administration, the rat was administered with ethanol in a dose of 6 g/kg body weight. Four hours and thirty minutes after the administration of ethanol, the rat was etherized, and blood was sampled from its heart to determine alcohol level in the blood by a alcoholic dehydrogenase method. For control, a physiological saline solution was used instead of the UDP-2Na solution.

The results are shown in Table 4 from which the alcohol level in blood of the rat administered with UDP-2Na is significantly lowered in comparison with the control.

Further, it was found that the alcohol level in blood almost completely correlates closely with the changes in behavior symptoms.

Table 4

| Group | Test Animal Number | Ethanol level in Blood (mg/ml) | Behavior |
|---|---|---|---|
| Control | 1 | 1.05 | normal walking |
| | 2 | 2.94 | deep sleep, lying on the side |
| | 3 | 3.09 | " |
| | 4 | 3.87 | " |
| | 5 | 3.48 | " |
| | 6 | 2.79 | " |
| | 7 | 2.79 | " |
| | 8 | 3.24 | " |
| | 9 | 4.18 | " |
| | Average | 3.05±0.84 | |
| UDP . 2Na Administration | 1 | 2.11 | normal walking |
| | 2 | 1.77 | " |
| | 3 | 0.57 | " |
| | 4 | 0.24 | " |
| | 5 | 0.75 | " |
| | 6 | 2.10 | " |
| | 7 | 1.08 | " |
| | 8 | 1.35 | " |
| | 9 | 1.72 | " |
| | 10 | 1.50 | " |
| | 11 | 2.16 | lying flat |
| | 12 | 2.74 | deep sleep |
| | Average | 1.51±1.09* | |

*Confidence Limits: 98%

EXAMPLE 5

Preparation of Pharmaceutical Composition a. Capsules

Pulverized disodium uridine-5'-diphosphate (300 g) was thoroughly mixed with lactose (98 g) and magnesium stearate (2 g), and hard gelatin capsules (No. 1) were filled with 400 mg each of the mixture.

b. Powder

Pulverized disodium uridine-5'-diphosphate (250 g) was thoroughly mixed with lactose (149 g) and magnesium stearate (1 g) to obtain a powder.

c. Tablets i. Pulverized disodium uridine-5'-diphosphate (100 g) was thoroughly mixed with lactose (46 g), crystalline cellulose (27 g), corn starch (5 g) and magnesium stearate (2 g). The mixture was formed by a tablet machine into tablets each 8 mm in diameter and weighing 180 mg.

ii. Pulverized disodium uridine-5'-diphosphate passed through 50 mesh screen (200 g), was mixed with lactose (173 g) and calcium carboxymethylcellulose (20 g). To the mixture was added an aqueous paste of 4 g of corn starch followed by kneading it to form dough. The dough was fed to an extrusion type granulator to form granules. After drying the granules, they were passed through 14 mesh of screen and mixed with magnesium stearate (3 g). The mixture was formed by a tabletting machine into tablets each weighing 200 mg and being 8 mm in diameter.

d. Parenteral Injections

Monopotassium phosphate (3.6 g), disodium phosphate in the form of $Na_2HPO_4.12H_2O$ (14.4 g) and disodium uridine-5'-diphosphate (60 g) were dissolved in distilled water for parenteral injection (1 lit.), and the solution was charged in colorless ampules each 2 ml in volume. The ampules charged were melt-sealed and after the ampules were melt-sealed, sterilized at 100° C for 30 minutes. The resulting parenteral injection which contained approximately 50 mg/ml of disodium uridine-5'-diphosphate and had a pH 7.0 did not cause any pain on administration.

What is claimed is:

1. A method for reducing the alcohol content or slowing the rate of increase thereof in the blood and inhibiting the accumulation of neutral lipid in the liver of human beings, which comprises administering to human beings, orally or parenterally, a pharmaceutical composition comprising an effective amount of a uridine diphosphate as an effective ingredient and a pharmaceutically acceptable carrier.

2. A method as set forth in claim 1 wherein said pharmaceutical composition is administered to human beings orally in the form of tablet, granule, powder, capsule, suspension or lemonade.

3. A method as set forth in claim 1 wherein the administration of said uridine diphosphate is made orally in a dose of from 10 to 5,000 mg per dose.

4. A method as set forth in claim 1 wherein the administration of said uridine diphosphate is made orally in a dose of from 50 to 500 mg per dose.

5. A method as set forth in claim 1 wherein the administration of said uridine diphosphate is made parenterally in a dose of from 10 to 1,000 mg per dose.

6. A method as set forth in claim 1 wherein the administration of said uridine diphosphate is made parenterally in a dose of from 50 to 500 mg per dose.

7. A method as set forth in claim 1 wherein the uridine diphosphate is the free form of uridine-5'-diphosphate or a metallic salt thereof.

8. A method as set forth in claim 7 wherein said metallic salt of uridine-5'-diphosphate is selected from the group consisting of sodium, potassium and lithium salts.

9. A method as set forth in claim 1 wherein the uridine diphosphate is the free form of uridine-3'-diphosphate or a metallic salt thereof.

10. A method as set forth in claim 9 wherein said metallic salt of uridine-3'-diphosphate is selected from the group consisting of sodium, potassium and lithium salts.

11. A method for slowing the rate of alcohol level increase in the blood and inhibiting the accumulation of neutral lipids in the liver, which comprises orally administering a pharmaceutical composition comprising an effective amount of uridine diphosphate as an active ingredient and a pharmaceutically acceptable carrier just before or at the time of intake of alcoholic drinks.

12. A method for slowing the rate of alcohol level increase in the blood and inhibiting the accumulation of neutral lipids in the liver, which comprises intravenously or intramuscularly injecting a pharmaceutical composition in the form of parenteral injection comprising an effective amount of a uridine diphosphate as an active ingredient and a pharmaceutically acceptable carrier just before or at the time of intake of alcoholic drinks.

13. A method for reducing the alcohol content of the blood and the accumulation of neutral lipid in the liver, which comprises orally administering to a patient suffering from alcoholism a pharmaceutical composition comprising an effective amount of a uridine diphospate as an active ingredient and a pharmaceutically acceptable carrier.

14. A method as set forth in claim 13 wherein said pharmaceutical composition is administered several times a day, the total amount per day being a maximum of 300 mg/kg. body weight based on the active ingredient.

15. A method for reducing the alcohol content of the blood and the accumulation of neutral lipid in the liver, which comprises intravenously or intramuscularly administering to a patient suffering from alcoholism a pharmaceutical composition for the prevention and treatment of alcoholism in the form of parenteral injection comprising an effective amount of a uridine diphosphate as an active ingredient and a pharmaceutically acceptable carrier.

16. A method as set forth in claim 15 wherein said pharmaceutical composition is administered at several times a day the total amount per day being a maximum of 30 mg/kg. body weight based on the active ingredient.

* * * * *